US012788607B1

(12) United States Patent
Romo

(10) Patent No.: US 12,788,607 B1
(45) Date of Patent: Nov. 10, 2026

(54) BACK BRACE WITH PADDED SLEEVE

(71) Applicant: Aspen Medical Products, LLC, Irvine, CA (US)

(72) Inventor: Albert V. Romo, Lakewood, CA (US)

(73) Assignee: Aspen Medical Products, LLC, Irvine, CA (US)

( * ) Notice: Subject to any disclaimer, the term of this patent is extended or adjusted under 35 U.S.C. 154(b) by 0 days.

(21) Appl. No.: 18/942,239

(22) Filed: Nov. 8, 2024

Related U.S. Application Data

(62) Division of application No. 17/687,562, filed on Mar. 4, 2022, now Pat. No. 12,138,192.

(60) Provisional application No. 63/157,597, filed on Mar. 5, 2021.

(51) Int. Cl.
*A61F 5/02* (2006.01)

(52) U.S. Cl.
CPC .............. *A61F 5/028* (2013.01); *A61F 5/024* (2013.01)

(58) Field of Classification Search
CPC .......... A61F 5/02–03; A61F 5/30; A61F 5/32; A61F 5/024; A61F 5/028; A41D 13/0531; A47C 7/36; A47C 7/40; A47C 7/402; A61G 7/07; A61G 13/1225; A61H 1/0292
USPC ........................................................ 602/5, 19
See application file for complete search history.

(56) References Cited

U.S. PATENT DOCUMENTS

| | | | | | |
|---|---|---|---|---|---|
| 4,475,543 | A * | 10/1984 | Brooks | A61F 5/028 602/19 |
| 5,499,965 | A * | 3/1996 | Sanchez | A61F 5/028 128/100.1 |
| 9,636,247 | B2 | 5/2017 | Miller et al. | |
| 12,138,192 | B1 | 11/2024 | Romo | |
| 2004/0220503 | A1 | 11/2004 | Kozersky | |
| 2008/0045873 | A1 * | 2/2008 | Zours | A61F 5/028 602/19 |
| 2008/0262401 | A1 * | 10/2008 | Wagner | A61F 5/028 602/19 |
| 2009/0045656 | A1 | 2/2009 | Chen et al. | |
| 2009/0163841 | A1 | 6/2009 | Garth | |

(Continued)

FOREIGN PATENT DOCUMENTS

WO WO-2007027573 A2 * 3/2007 ............. A61F 5/026

OTHER PUBLICATIONS

EP22764208.9 filed May 10, 2023 Partial European Search Report dated Dec. 23, 2024.

(Continued)

*Primary Examiner* — Keri J Nelson
*Assistant Examiner* — Seth R. Brown
(74) *Attorney, Agent, or Firm* — Rutan & Tucker, LLP

(57) ABSTRACT

A sleeve for covering an external surface of an orthosis is described, where the orthosis includes an adjustable posterior frame featuring a first panel slidably coupled to a second panel. The sleeve includes (i) a first material forming an anterior side of the sleeve; (ii) a second material forming a posterior side of the sleeve; (iii) a first padded area attached to a first region of an inner surface of the first material partially forming the anterior side of the sleeve, (iv) a second padded area attached to a second region of an inner surface of first material partially forming the anterior side of the sleeve, and (v) an elastic middle area of the second material interposed between an upper area of the second material proximate to the first padded area and a lower area of the second material proximate to the second padded area.

12 Claims, 7 Drawing Sheets

(56) References Cited

U.S. PATENT DOCUMENTS

| | | | |
|---|---|---|---|
| 2011/0105971 A1 | 5/2011 | Ingimundarson et al. | |
| 2011/0114101 A1 | 5/2011 | Tweardy et al. | |
| 2012/0253251 A1 | 10/2012 | Thornton | |
| 2013/0261521 A1 | 10/2013 | Carter | |
| 2014/0305982 A1 | 10/2014 | Pelland et al. | |
| 2015/0290019 A1 | 10/2015 | Garth et al. | |
| 2016/0081841 A1* | 3/2016 | Miller | A61F 5/024 602/19 |
| 2018/0303699 A1 | 10/2018 | Romo et al. | |
| 2018/0317634 A1 | 11/2018 | Rittenhouse et al. | |
| 2019/0091094 A1* | 3/2019 | Romo | B25J 9/0006 |
| 2020/0103073 A1 | 4/2020 | Lennings et al. | |
| 2020/0179153 A1 | 6/2020 | Wang | |
| 2022/0280324 A1 | 9/2022 | Romo et al. | |

OTHER PUBLICATIONS

U.S. Appl. No. 17/687,562, filed Mar. 4, 2022 Non-Final Office Action dated Dec. 26, 2023.
U.S. Appl. No. 17/687,562, filed Mar. 4, 2022 Notice of Allowance dated Jun. 7, 2024.
U.S. Appl. No. 17/687,562, filed Mar. 4, 2022 Restriction Requirement dated Jul. 5, 2023.
U.S. Appl. No. 17/687,574, filed Mar. 4, 2022 Notice of Allowance dated Sep. 13, 2024.
EP22764208.9 filed May 10, 2023 Extended European Search Report dated Apr. 9, 2025.

* cited by examiner

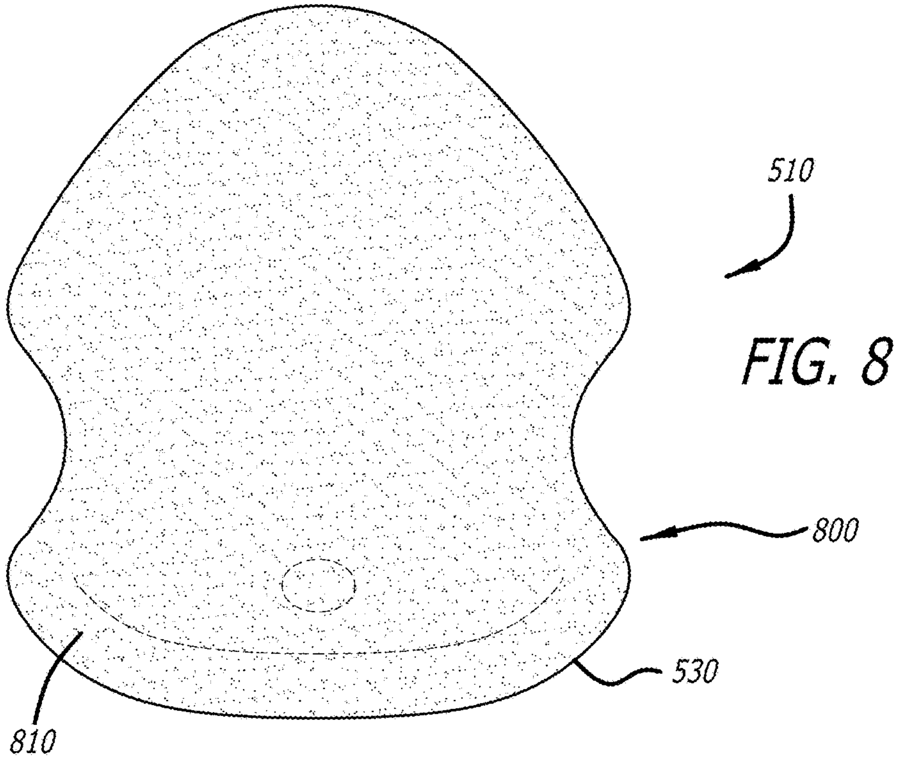
FIG. 8
FIG. 9
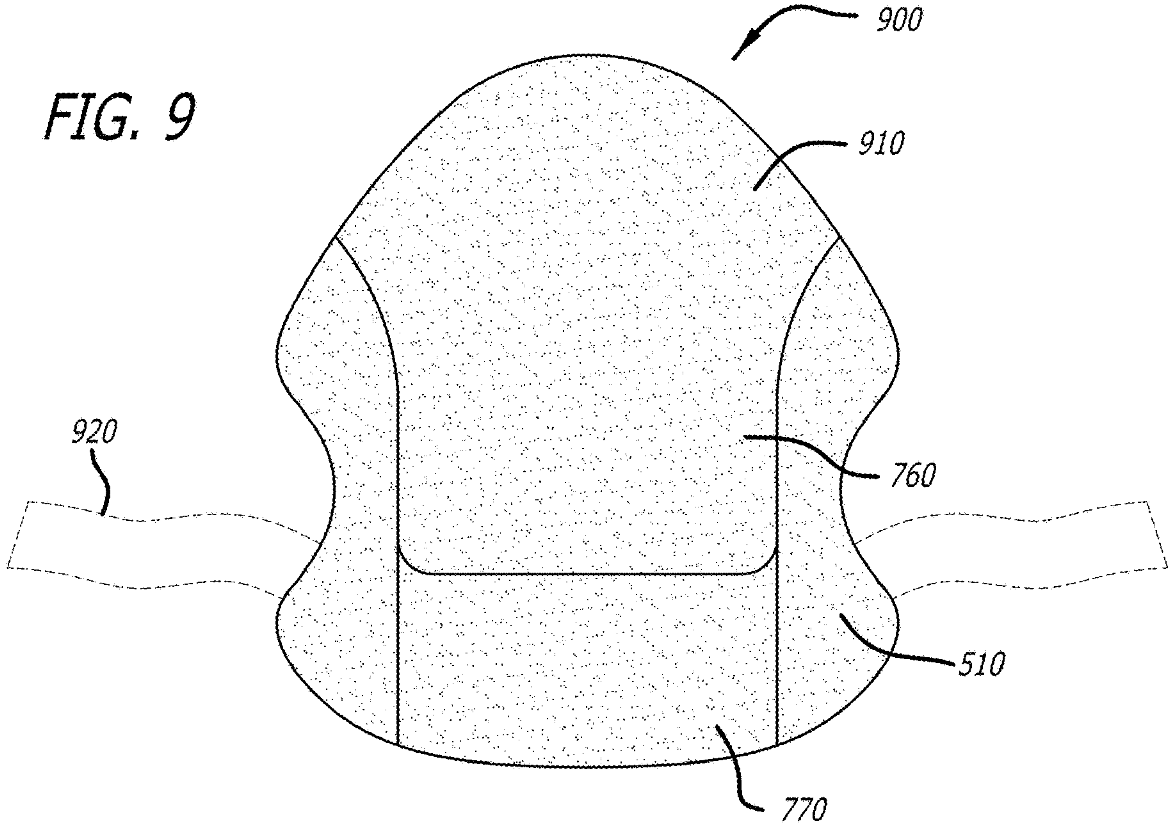

BACK BRACE WITH PADDED SLEEVE

CROSS-REFERENCE TO RELATED APPLICATIONS

This application is a divisional application of U.S. patent application Ser. No. 17/687,562 filed Mar. 4, 2022, now U.S. Pat. No. 12,138,192 issued Nov. 12, 2024, which claims benefit of U.S. Provisional Patent Application No. 63/157,597 filed Mar. 5, 2021, the entire contents of which is incorporated by reference herein.

FIELD

The field of the invention is a size (e.g., height and/or width) adjustable back braces.

BACKGROUND

The background description includes information that may be useful in understanding aspects of the invention. It is not an admission that any of the information provided herein is prior art or relevant to the presently claimed invention, or that any publication specifically or implicitly referenced is prior art.

These and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

Back braces are often used by users for support. Currently, back braces are manufactured and distributed by taking into account governmental coding and reimbursement procedures that encourage off-the-shelf products with minimal skews and products that target a large number of patients. At this time, governmental coding and reimbursement procedures encourage back braces to be sized to accommodate an "average-sized" male (e.g., approximately the seventy-fifth (75th) percentile male). While posterior panels of the brace braces are sized to properly fit an average sized male, there are many patients for whom the back brace is improperly sized due to their physical characteristics, such as petite (5'3" and under) or a tall (6'4" and over) patients, patients with extremely long or short torsos, or the like.

Even if the posterior panels for back braces were adjustable, conventional padding techniques used for these back braces fail to accommodate for adjustments made to the back brace. As a result, clinicians are required to alter the installed padding for provide better comfort in wearing the back brace, which is labor intensive and difficult to scale when supporting greater numbers of patients.

BRIEF DESCRIPTION OF THE DRAWINGS

FIG. 8 is a perspective view of an anterior side of the adjustable posterior frame encapsulated by the padded sleeve.

FIG. 9 is a perspective view of a posterior side of the adjustable posterior frame encapsulated by the padded sleeve.

DETAILED DESCRIPTION

The following discussion provides example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Also, as used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

Moreover, and unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

I. Summary

Figure 2A:
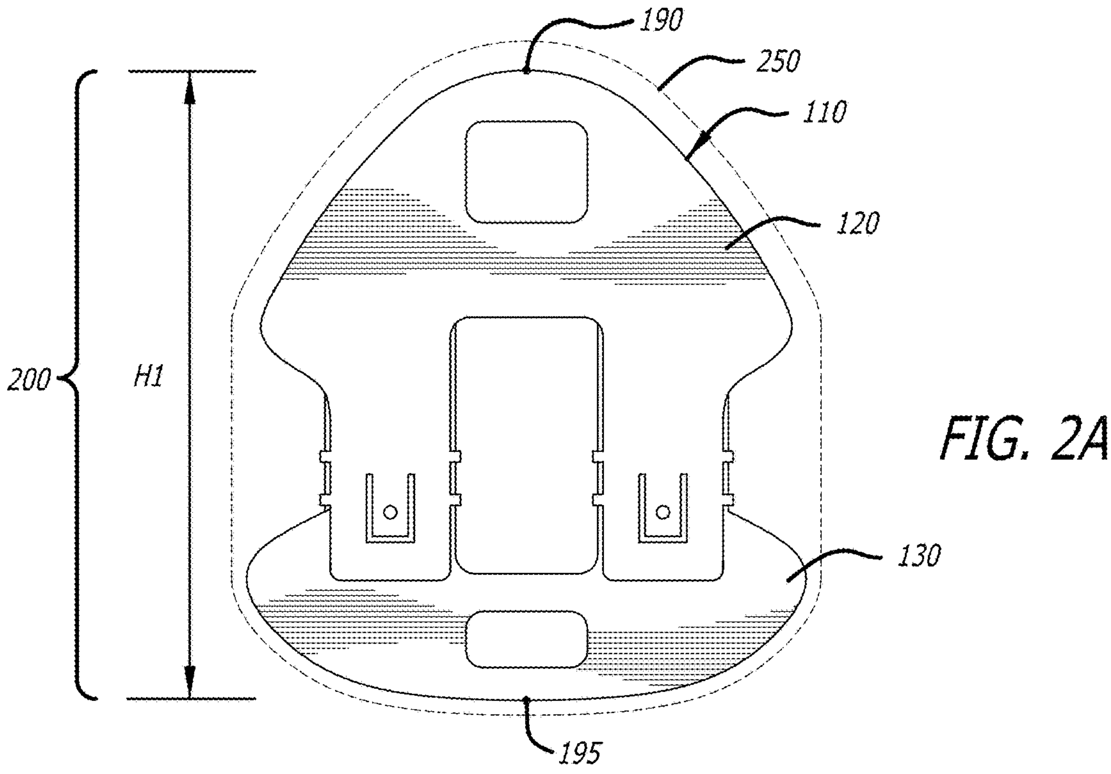
FIG. 2A is a perspective view of the multi-panel, adjustable posterior frame of FIG. 1 positioned in a first state of operation.
Figure 2B:
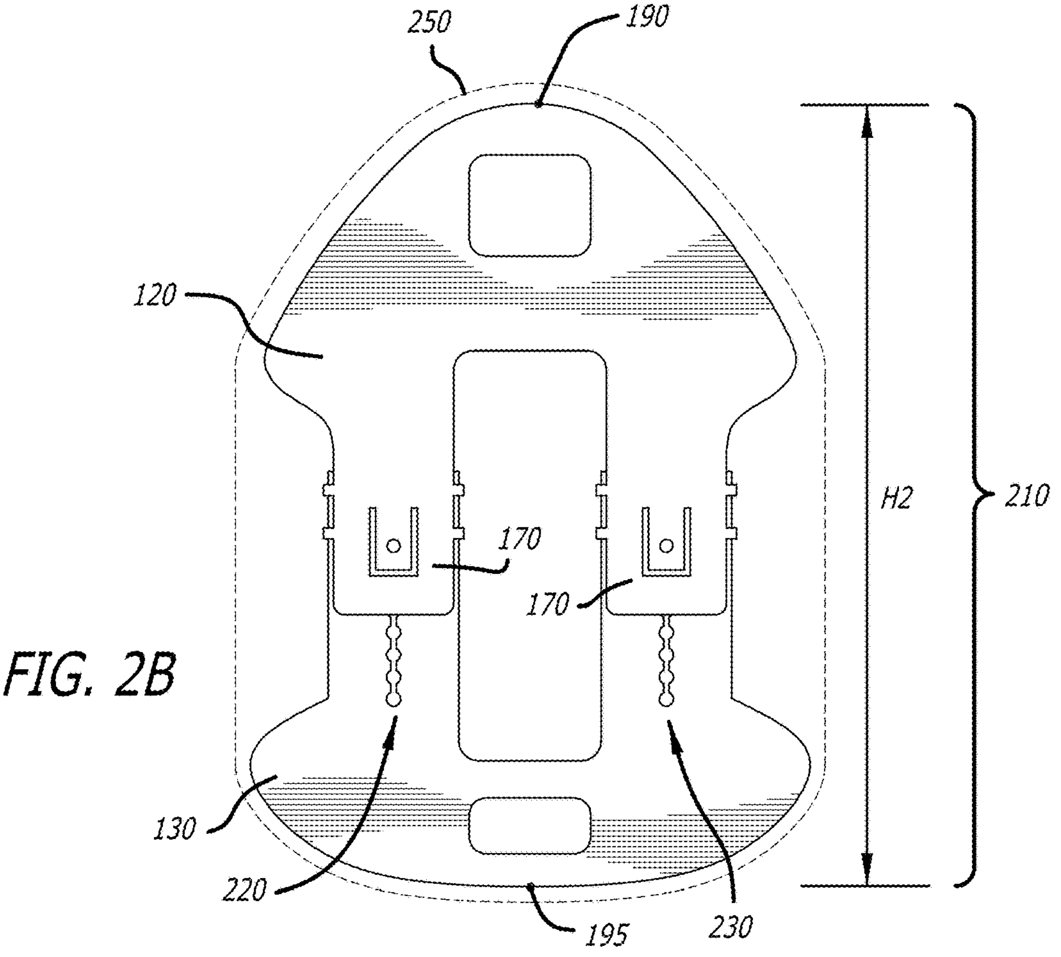
FIG. 2B is perspective view of the multi-panel, adjustable posterior frame of FIG. 1 positioned in a second state of operation.

Embodiments of the invention are directed to an height and/or width adjustable orthosis, such as a back brace for example. According to a first embodiment of the disclosure, the back brace features a belt permanently or removably attached to a multi-panel adjustable posterior frame, where the adjustable posterior frame features a first panel and a second panel. Herein, at least one panel (e.g., first panel) configured to move superiorly and inferiorly relative to the other panel (e.g., second panel). A slot, defined as channel or an elongated open groove, is at least partially formed by the first panel and the second panel. A pad may be disposed within the slot, where the pad features a particular size and dimension to cover the slot formed between the first (upper) and second (lower) panels. As a result, at least one of the first and second panels can slide relative to the pad such as the slidable configuration as illustrated in FIGS. 2A-2B and described below.

Figure 3A:
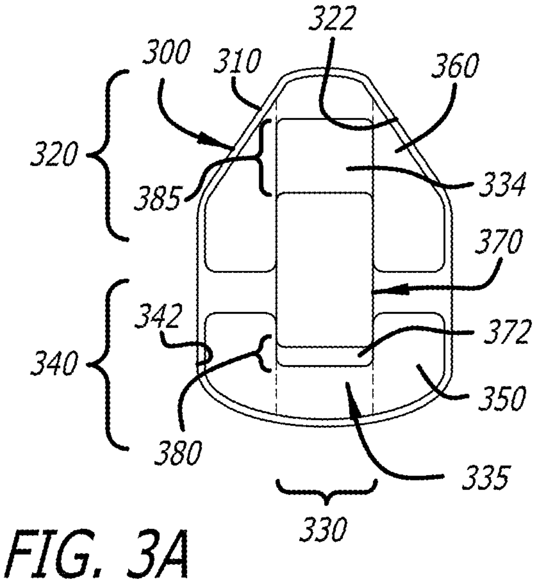
FIGS. 3A-3B are perspective views of a first embodiment of a padding locations on the multi-panel, adjustable posterior frame of FIG. 1 to illustrate padding overlap to maintain the padding at prescribed locations independent of height adjustment of the posterior frame.
Figure 3B:
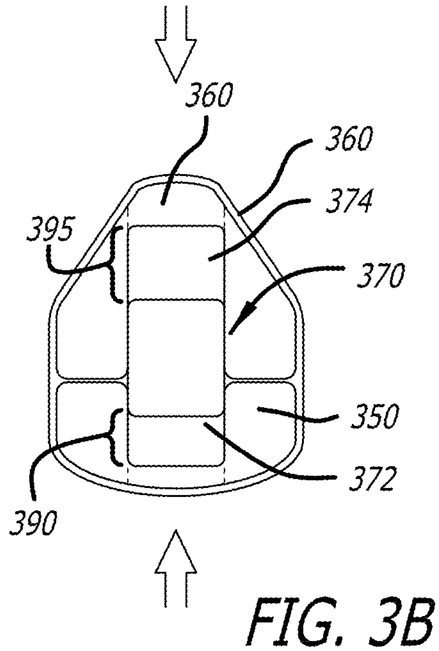

It is further contemplated that a sleeve may be sized and dimensioned to cover the adjustable posterior frame for any selected height position as illustrated in FIGS. 3A-3B. Padding may be disposed within the sleeve. The pad can be positioned to be horizontally centered about the sleeve. Additionally, the sleeve can be affixed to the first and second panels.

Based on this first embodiment, the upper padding of the sleeve may be attached to an upper portion of a sleeve cover. Similarly, the lower padding of the sleeve may be attached to a lower portion of the sleeve cover, where the central pad may be attached to a center of the sleeve cover. Therefore, by attaching the upper padding to the upper portion of the sleeve cover as well as the lower padding to the lower portion of the sleeve cover, the padding is configured to move together to accommodate the sizing adjustments made to the back brace. Elastic (stretchy) material is located at the center area of the sleeve cover to allow the padding to extend to accommodate height variances as the first (upper) panel is moved superiorly or inferiorly relative to the second (lower) panel.

According to second embodiment of the disclosure, the size (height) adjustable orthosis (e.g., back brace) comprises a belt attached to the dual-panel adjustable posterior frame described below. More specifically, the adjustable posterior frame features a first (upper) panel and a second (lower) panel, where the first panel partially overlays and is slidably engaged with the second panel. According to this embodiment of the disclosure, the first panel features a first set of fasteners and the second panel features a plurality of locking members, including at least a first set of locking members and a second set of locking members. Herein, the "set of fasteners" constitutes one or more fasteners while each of the "first set of locking members" and the "second set of locking members" constitutes one or more locking members configured and sized to receive the corresponding set of fasteners. For embodiments described herein, the first and second panels are configured to move vertically (superiorly or inferiorly) relative to each other, and once set to a desired collective height, the set of fasteners is set to engage with a complementary set of locking members, such as, for example, (1) the first set of locking members when a first height position is selected or (2) the second set of locking members when a second height position is selected.

It is contemplated that each of the first set of fasteners may include, but is not limited or restricted to a flexible tab, a lock screw, a latch, or any other fastening device. The operating state of the fastener(s) is controlled by a fastener adjustment guide. Herein, the fastener adjustment guide may be configured as a guide wire that is physically coupled to the set of fasteners and configured to place each fastener into a locked state or an unlocked state. More specifically, when placed into a first operating state, the fastener adjustment guide allows each fastener to enter into a locked state. Upon placement into a second operating state, the fastener adjustment guide causes each fastener to enter into an unlocked state. An "unlocked" state is achieved by the fastener adjustment guide recoiling the fastener(s), which causes a protrusion for each fastener located in the first panel to disengage from its corresponding locking member located in the second panel. In response to releasing the fastener adjustment guide to return to its first operating state, each protrusion for the set of fasteners may engage with a corresponding locking member that may be positioned higher on the second panel when the height of the posterior brace is increased or positioned lower on the second panel when the height of the posterior brace is decreased.

Given that the posterior frame is adjustable, a technique is needed to ensure that the pads/padding are properly positioned on an anterior side of the adjustable posterior frame regardless of the selected height of the posterior frame. This may be accomplished by placement of the pads at particular locations of an anterior side of the second panel prior to encapsulation of the padded, adjustable posterior frame within a padded sleeve.

The padded sleeve features a sleeve cover including an anterior (front) cover section and a posterior (back) cover section. The anterior cover section includes an upper region, a middle region and a lower region. According to one embodiment of the disclosure, for the anterior cover section, a first padding is attached to an inner surface of the lower region and a second padding is attached to an inner surface of the upper region. Additionally, the middle region of the anterior cover section may be formed with an elastic (stretchy) material to allow the anterior cover section to extend to accommodate height variances as the first (upper) panel is moved superiorly or inferiorly relative to the second (lower) panel.

A perimeter of the posterior cover section is physically coupled to or is integrated as an extension of the anterior cover section. The posterior cover section of the sleeve cover also includes an upper region, a middle region and a lower region. According to this embodiment of the disclosure, the middle region provides an opening that provides access to a compartment formed by inner surface of the anterior cover section and the of the posterior cover section. The opening is sized for insertion of the adjustable posterior frame, including installed pads, into the compartment. This allows for the adjustable posterior frame to reside within the compartment to protect the posterior frame from environmental conditions.

A first closing flap is attached to an upper region of the sleeve cover and a second closing flap is attached to a lower region of the sleeve cover. Both closing flaps are arranged to fold towards the opening, where the first closing flap covers the opening or at least a majority portion of the opening. Fasteners are attached to end portions of these closing flaps to secure the closing flaps together after the adjustable posterior frame is placed within the component, where the first and second paddings are positioned anteriorly from the inserted, adjustable posterior frame. The sleeve allows access and removal (for resizing) of the posterior frame from the padded sleeve upon disengaging the closing flaps providing a clinician or patient access to the posterior frame through the opening.

II. Size (Height) Adjustable Orthosis

Figure 1:
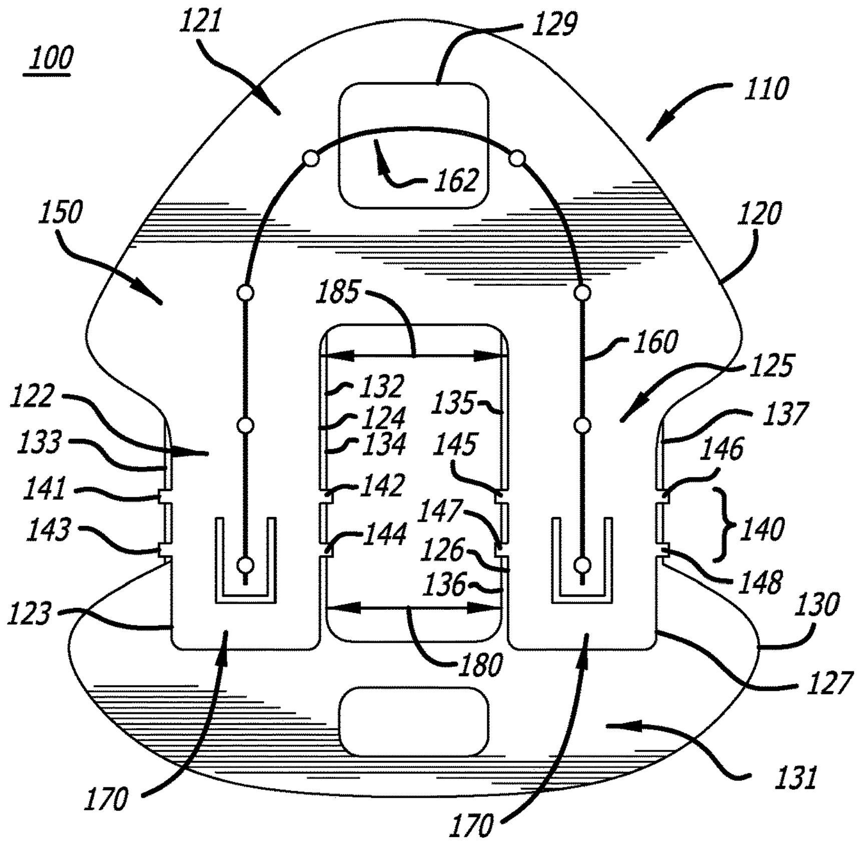
FIG. 1 is a perspective view of an embodiment of an orthosis featuring a multi-panel adjustable posterior frame along with size (height) adjustment fasteners operating in cooperation with a fastener adjustment guide wire.

Referring to FIG. 1, an embodiment of an orthosis 100 featuring an adjustable posterior frame 110, which includes multiple (e.g., two or more) panels that are slidably engaged and partially controlled by a fastener adjustment guide 160, is shown. The adjustable posterior frame 110 includes (i) a first panel 120 featuring an upper area 121 and first pair of columns 122 and 125; (ii) a second panel 130 featuring a lower area 131 and a second pair of columns 132 and 135; (iii) a plurality of panel guide elements 140 (e.g., panel guide elements 141-148); and (iv) a fastening mechanism 150. According to this embodiment of an adjustable posterior frame, the fastening mechanism 150 further includes a fastener adjustment guide 160 adapted to allow a clinician to partially disengage the first panel 120 from the second panel 130.

Herein, the panel guide elements 141-148 extend from the first panel 120 to engage with a plurality of edges of the second panel 130. As an illustrative example, the first panel 120 may be positioned posteriorly to the second panel 130, where a first set of guide elements 141 and 143 extend from a first edge 123 of the first column 122 of the first panel 120 to engage with a first edge 133 of the first column 132 of the second panel 130. A second set of guide elements 142 and 144 extend from a second edge 124 of the first column 122 of the first panel 120 to engage with a second edge 134 of the first column 132 of the second panel 130. Similarly, a third set of guide elements 145 and 147 extend from a first edge 126 of a second column 125 of the first panel 120 to engage with a first edge 136 of the second column 135 of the second panel 130, while a fourth set of guide elements 146 and 148 extend from a second edge 127 of the second column 125 of the first panel 120 to engage with a second edge 137 of the second column 135 of the second panel 130.

According to one embodiment of the disclosure, the panel guide elements 141-148 are configured to maintain a slidable connection between the first panel 120 and the second panel 130. This slidable connection allows the first panel 120 to be adjusted and secured to the second panel 130 using the fastening mechanism 150. Hence, the posterior frame 110 of the orthosis 100 may be adjusted to the patient's anatomy instead of a predetermined posterior back panel height.

According to one embodiment of the disclosure, the fastening mechanism 150 includes height adjustment fasteners 170, which may be deployed at one or more regions within columns 122 and 125 of the first panel 120. The height adjustment fasteners 170 may correspond to a number of different fastener types, such as a flexible lift tabs as shown, which are physically coupled to complementary locking members (not shown) implemented within the second panel 130 when the height adjustment fasteners 170 are placed into a locked state.

Additionally, the height adjustment fasteners 170 are mechanically coupled to the fastener adjustment guide 160, namely a wire that, in response to tensioning forces (e.g., upward, downward, inward, and/or outward) being placed thereon to activate the fastener adjustment guide 160 (e.g., pulling upward), the height adjustment fasteners 170 are placed into an unlocked state by disengaging from their complementary locking members. Otherwise, as a default, the height adjustment fasteners 170 remain in a locked state Referring still to FIG. 1, the first panel 120 includes the upper area 121 with the first column 122 and the second column 125 extending downward (when worn) from the upper area 121. The upper area 121 is triangular-shaped as this portion of the adjustable posterior frame 100 may operate as a headrest for some patients or an upper back support for other patients. A first spacing 180 is provided between the first column 122 and the second column 125 of the first panel 120 while a second spacing 185 is provided between the first column 132 and the second column 135 of the second panel 130. The fastener adjustment guide (wire) 160 is routed over a portion of the first column 122, the upper area 121 and a portion of the second column 125 to interconnect the height adjustment fasteners 170. As shown, the fastener adjustment guide 160 is accessible along the first and second columns 122 and 125 as well as within the upper area 121. However, it is contemplated that the first panel 120 may be configured with a thickness to conceal most of the fastener adjustment guide 160 so that only a segment 162 of the fastener adjustment guide 160 is accessible through a slot 129 within the first panel 120.

Responsive to the tensioning force being applied to the segment 162 of the fastener adjustment guide 160, the height adjustment fasteners 170 are laterally adjusted to disengage from their counterpart locking members within the second panel 130. This enables the first panel 120 to move vertically (superiorly or inferiorly) relative to the second panel 130, changing from at least a first height to a second height.

As shown in FIGS. 2A-2B, a first height (H1) 200 of the posterior frame 110 can be a first vertical distance from an uppermost point 190 of the first panel 120 to a lowermost point 195 of the second panel 130. Additionally, a second height (H2) 210 is a second vertical distance from the uppermost point 190 of the first panel 120 to the lowermost point 195 of the second panel 130 after adjustment of a vertical height of the first panel 120. The second height H2 210 constitutes a greater vertical distance than the first height H1 200, given that the height adjustment fasteners 170 are connected to one of the sets of complementary locking members 220 and 230 positioned further away from the lower area 131 of the second panel 130. The posterior frame 110 is encapsulated by a padded sleeve shown by dashed lines 250 and illustrated in more detail in FIGS. 3A-4B and FIGS. 5-9.

III. Adjustable Padded Sleeve—First Embodiment

Referring now to FIGS. 3A-3B, perspective views of a first embodiment of a padded sleeve 300 adapted to encapsulate the adjustable posterior frame 110 of FIG. 1 are shown. Herein, the padded sleeve 300 includes a sleeve cover 310, which generally includes an upper region 320, a central region 330 and a lower region 340. According to one embodiment of the disclosure, a first padding 350 is attached to an inner surface 342 of the lower region 340 of the sleeve cover 310 for placement anteriorly (in front of) a substantial portion of the lower area 131 of the second panel 130 and a portion of an anterior side of the first and second columns 132 and 135 of the second panel 130 of FIG. 1. A second padding 360 is attached to an inner surface 322 of the upper region 320 of the sleeve cover 310 for placement anteriorly (in front of) a substantial portion of the upper area 121 of the first panel 120 and optionally a portion of an anterior side of the first and second columns 132 and 135 of the second panel 130 of FIG. 1.

Additionally, the central region 330 features a rectangular access window 335 formed in part by spacing between inner edges of the columns 122 and 125 of the first panel 120 and the columns 132 and 135 of the second panel 130. Herein, a pad 370 is positioned within the central region 330, where the pad 370 is sized to remain generally centralized within the central region 330. As shown, according to this embodiment of the disclosure, a first end 372 of the pad 370 overlaps the first padding 350 and a second end 374 of the pad 370 overlaps the second padding 360.

As shown, when the adjustable posterior frame is placed into a heightened state as shown in FIG. 3A, the central pad 370 overlaps a first prescribed amount of area 380 of the first padding 350 and a second prescribed amount of area 385 of the second padding 360. However, when the adjustable posterior frame is placed into a lower (or lowest) state, as shown in FIG. 3B, the first end 372 of the central pad 370 overlaps a third prescribed amount of area 390 of the first padding 350, where the third prescribed amount of area 390 is greater than the first prescribed amount of area 380. Also, as shown in FIG. 3B, the second end 374 of the central pad 370 overlaps a fourth prescribed amount of area 395 of the second padding 360, where the fourth prescribed amount of area 395 is less than or equal to the second prescribed amount of area 385.

Figure 4A:
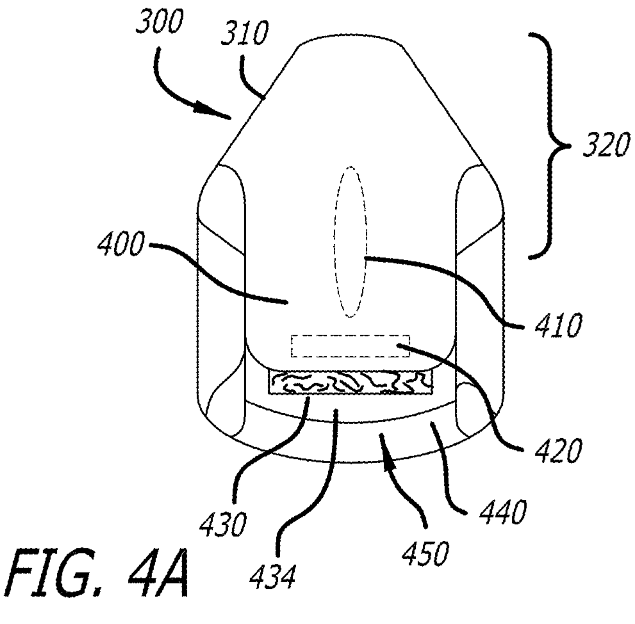
FIGS. 4A-4B are perspective views of a first embodiment of a posterior side of a padded sleeve sized and dimensioned to at least partially cover padding and portions of the first and second panels of the posterior frame.
Figure 4B:
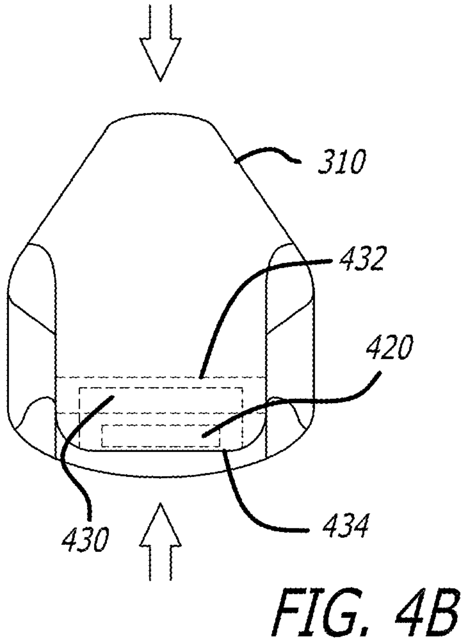

Referring to FIGS. 4A-4B, perspective views of a first embodiment of a posterior side of the padded sleeve 300 is shown, where the padded sleeve 300 is sized and dimensioned to cover the adjustable posterior frame 110 of FIG. 1. As shown in FIG. 4A, posterior side of the sleeve cover 310 features at least first closing flap 400 attached to the upper region 320 of the sleeve cover 310. The closing flap 400 is arranged to fold towards and cover an opening 410 within the sleeve cover 310 to enable the adjustable posterior frame 110 of FIG. 1 to be inserted therein. A first fastener 420 (e.g. hook fastener) may be attached to an end portion of the closing flap 400 and a second fastener 430 (e.g., loop fastener) may be attached to a posterior surface 440 of a posterior portion 450 of the sleeve cover 310. As a result, given the increased height of the adjustable posterior frame within the sleeve 300 as shown in FIG. 4A, the first fastener 420 associated with the closing flap 400 attaches to an upper end 432 of the second fastener 430. In contrast, as shown in FIG. 4B, when the padded sleeve 300 houses the adjustable posterior frame in a lowered state, the first fastener 420 associated with the closing flap 400 attaches to a lower end 434 of the second fastener 430.

IV. Adjustable Padded Sleeve and Deployment-Second Embodiment

Figure 5:
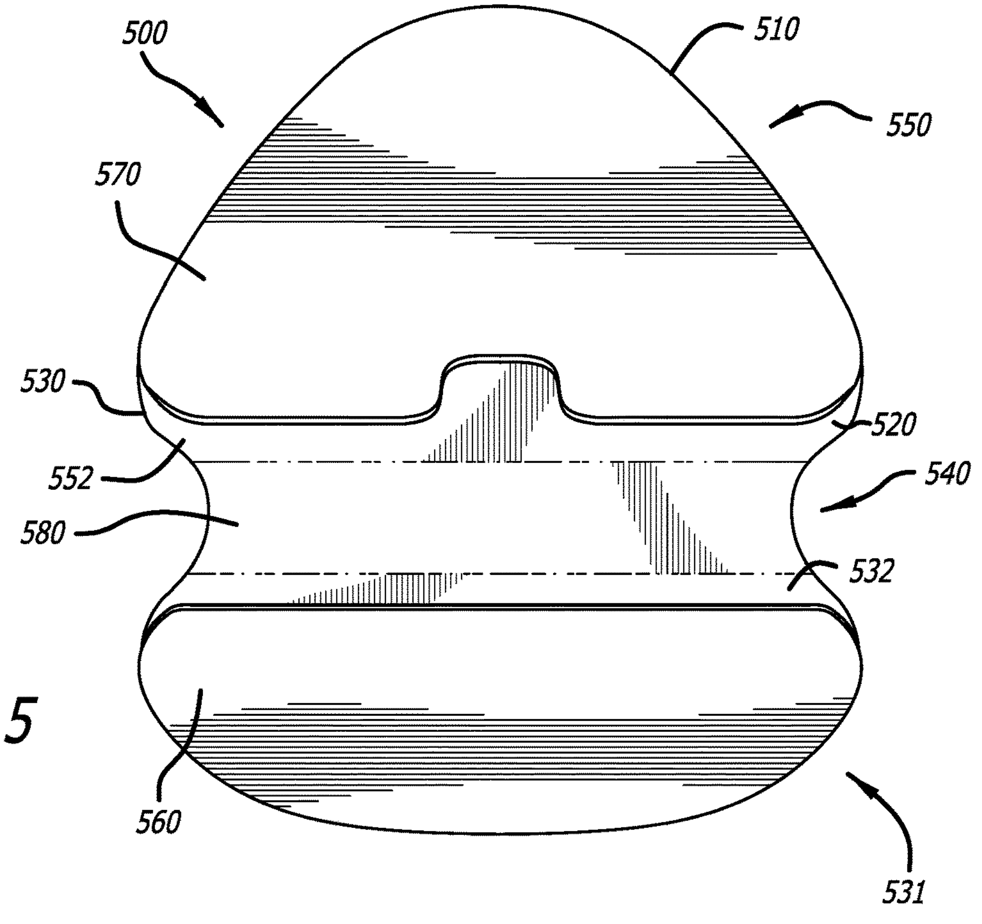
FIG. 5 is perspective view of a second embodiment of a padding architecture of the padded sleeve sized and dimensioned to encapsulate the adjustable posterior frame.

Referring now to FIG. 5, a perspective view of a second embodiment of a padding architecture 500 deployed on an anterior inner section 520 of a padded sleeve 510 sized and dimensioned to encapsulate the adjustable posterior frame 110 of FIG. 1 is shown. The anterior inner section 520 features a sleeve cover 530, which includes a lower cover region 531, a middle cover region 540, and an upper cover region 550. The lower cover region 531 features a first padding 560 attached to an inner surface 532 of the lower cover region 531 being part of the anterior inner section 520 of the padded sleeve 510. In some instances, the first region and the second region are formed of a first inelastic material.

According to this embodiment of the disclosure, the first padding 560 is positioned to reside between the sleeve cover 530 and the second panel 130 (e.g., lower area 131 and optionally portions of the columns 132/135 of the second panel 130). The upper cover region 550 features a second padding 570 attached to an inner surface 552 of the upper cover region 550 being part of the anterior inner section 520 of the padded sleeve 510. The second padding 570 is positioned to reside between the sleeve cover 530 and at least the upper area 121 of the first panel 130 (e.g., upper area 121 and optionally portions of the columns 132/135 of the second panel 130).

Additionally, the middle cover region 540 may be formed with an elastic (stretchy) material 580 to allow the anterior inner section 520 to vertically extend to accommodate for height variances of the adjustable posterior frame 110 as the first (upper) panel is moved superiorly or inferiorly relative to the second (lower) panel. This allows for the first padding 560 and second padding 570 to retain their positioning in connection with components of the adjustable posterior frame 110 regarding as to whether the adjustable posterior frame is placed in the first height position (H1) or the second height position (H2).

Although not shown in FIG. 5, the padded sleeve 510 features a posterior section that includes an opening that allows for the insertion of the adjustable posterior frame 110 of FIG. 1 to be inserted within a compartment formed within the padded sleeve 510. The posterior section is described below and illustrated in FIGS. 7A-7C.

Figure 6A:
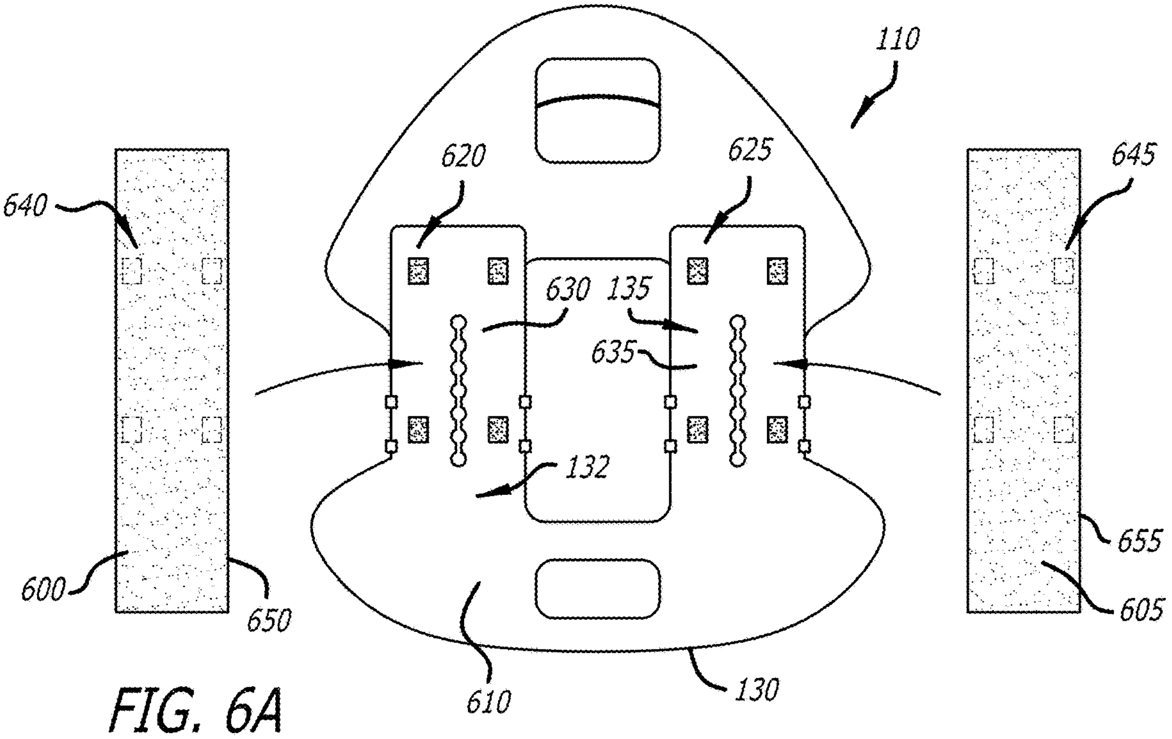
FIGS. 6A-6B are perspective views of a first set of pads attached to an anterior region of the second panel of the adjustable posterior frame.
Figure 6B:
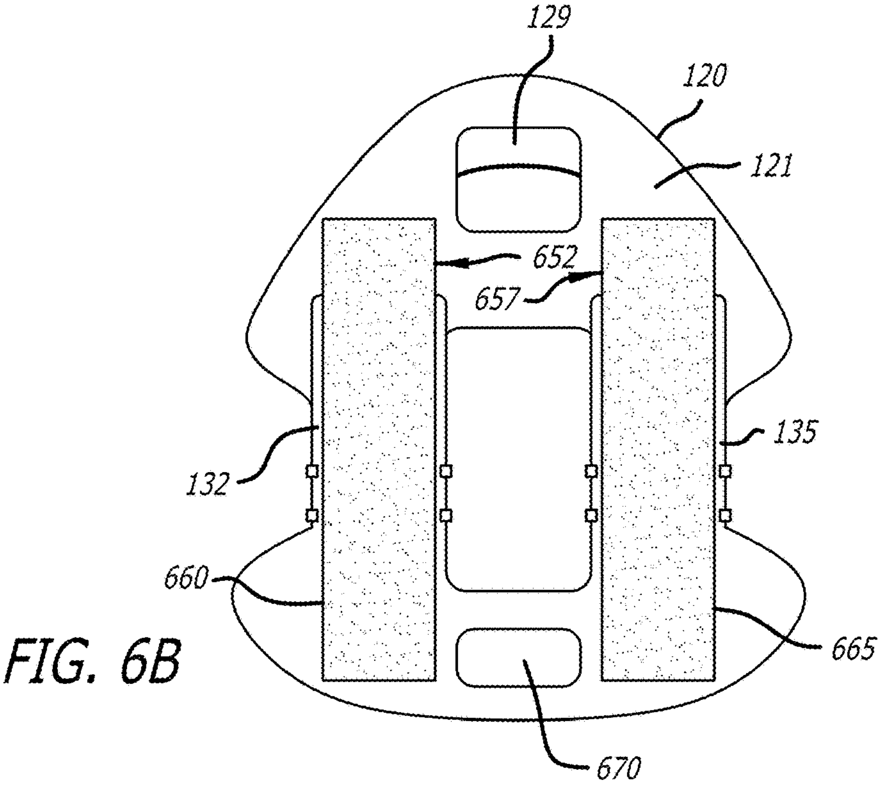

Referring to FIGS. 6A-6B, perspective views of a plurality of pads 600 and 605 attached to an anterior surface region 610 of the second panel 130 of the adjustable posterior frame 110 is shown. Herein, as shown in FIG. 6A, the second panel 130 features the first column 132 and the second column 135, each including one or more fasteners 620/625 (e.g., unbroken loop "UBL", hook, female snap, male snap, etc.) mounted on an anterior sides 630/635 of the columns 132/135. Each of the pads 600/605 includes one or more fasteners 640/645 (e.g., hook, UBL, male snap, female snap, etc.) mounted on posterior sides 650/655 of the pads 600/605. The fastener(s) 640/645 are complementary (and configured for attachment) to fastener(s) 620/625 mounted on the columns 132/135.

After being attached to the second panel 130, as shown in FIG. 6B, the pads 600/605 may cover a targeted portion or a substantial (e.g., greater than 50%) of the corresponding first and second columns 132/135 and first distal ends 652/657 of the pads 600/605 extend over portions of the upper area 121 of the first panel 120. Additionally, second distal ends 660/665 of the pads 600/605 extend portions of the lower area 131 of the second panel 130. According to this embodiment of the disclosure, the pads 600/605 avoid covering a rectangular access window 660 partially formed by the edges of the columns 122/132 & 125/135, the slot 129 deployed within the upper area 121 and another slot 670 deployed within the lower area 131.

Figure 7A:
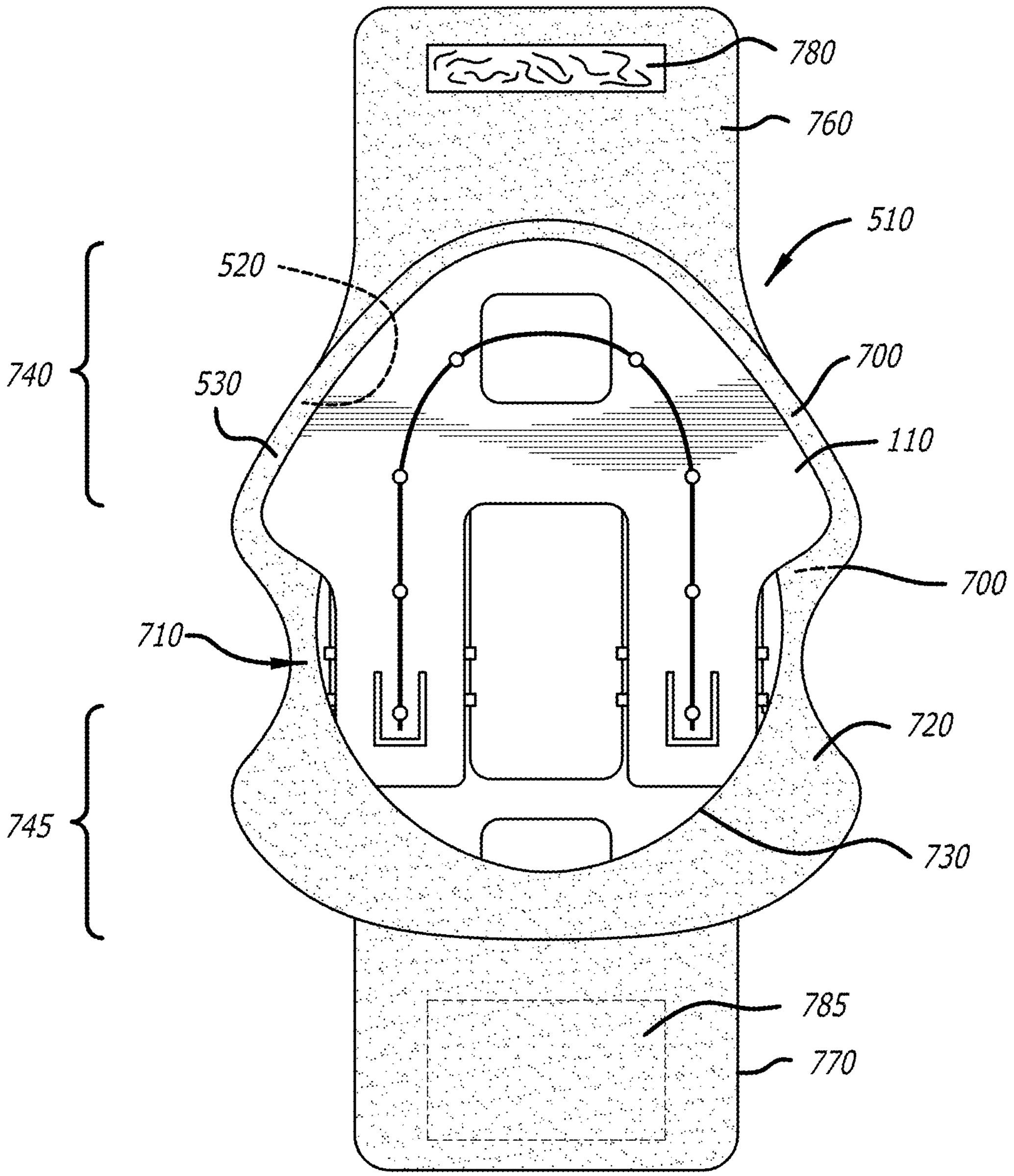
FIGS. 7A-7C are perspective views of the installation of the padded sleeve positioned over the padded, adjustable posterior frame as shown in FIG. 6B.
Figure 7B:
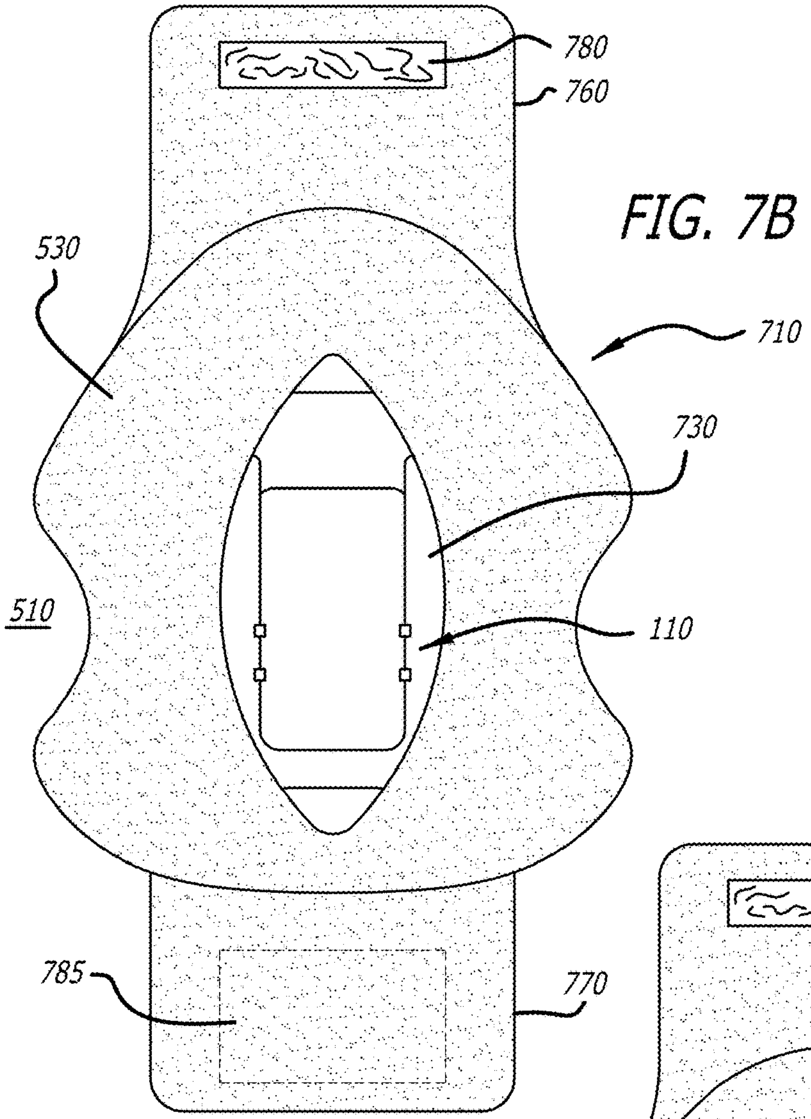
Figure 7C:
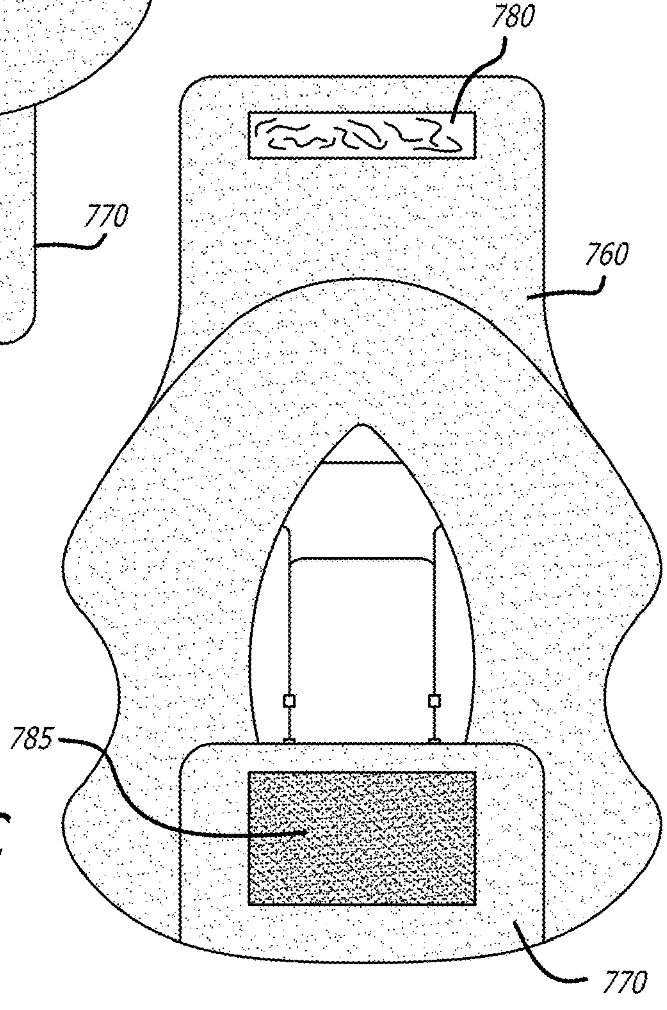

Referring now to FIGS. 7A-7C, perspective views of the installation of the padded sleeve 510 arranged to encapsulate the adjustable posterior frame 110 is shown. Herein, the padded sleeve 510 features the sleeve cover 530 that includes an anterior cover section 700 and a posterior cover section 710. As described above and illustrated in FIG. 5, the anterior cover section 700 includes the anterior inner section 520 with a sheet of material constituting the anterior outer section 720.

The posterior cover section 710 includes an opening 730 formed between and partially within an upper region 740 and a lower region 745 of the posterior cover section 710. According to one embodiment of the disclosure, as shown in FIG. 7A, the upper and lower regions 740 and 745 may be made of an elastic material to allow for the opening 730 to be stretched and expanded in area to receive the adjustable posterior frame 110. Herein the adjustable posterior frame 110 is positioned with the first panel 120 facing posteriorly with the pads (not shown) attached to the second panel 130 are facing anteriorly. Thereafter, the opening 730 returns to its normal size as shown in FIG. 7B.

The posterior cover section 710 of the sleeve cover 530 also includes a first closing flap 760 extending from the upper region of the anterior cover portion 700 and a second closing flap 770 extending from the lower region of the anterior cover portion 700. Both closing flaps 760/770 are arranged to fold towards the opening 730. Fasteners 780/785 are attached to end portions of these closing flaps 760/770 to encapsulate the adjustable posterior frame 110 within the padded sleeve 510 where the first and second padding 560/570 are positioned anteriorly to the inserted adjustable posterior frame 110. The sleeve cover 530 allows access and removal (for resizing) of the adjustable posterior frame 110 upon disengaging the closing flaps 760/770, thereby providing a clinician or patient access to the posterior frame 110 through the opening 730. As shown in FIG. 7C, to account for changes in size, the fastener 785 is provided a larger surface area to account whether the closing flap 760 will extend over the opening 730 by a lesser amount when storing the posterior frame 110 at its heightened state than the length of extension over the opening 730 when the posterior frame 110 is set to its lowest state.

Referring to FIG. 8, a perspective view of an anterior side 800 of the adjustable posterior frame 110 of FIG. 1 encapsulated by the padded sleeve 510 is shown. Herein, an anterior surface 810 of the sleeve cover 530 is exposed, with the pads 600/605 and padding 560/570 of FIGS. 5A-6B adjacent to a posterior surface 910 of the sleeve cover 530 (see FIG. 9). As a result, when worn, the pads/padding (via the sleeve cover 530) are in contact with the patient's back.

Referring to FIG. 9, a perspective view of a posterior side 900 of an adjustable posterior frame 110 of FIG. 1 encapsulated by the padded sleeve 510 is shown. Herein, the posterior surface 910 of the sleeve cover 530 is exposed with the opening 730 covered by the first closing strap 760 being secured by the second closing strap 770. Although not shown in detail, a belt 920 may be permanently or removably attached to the multi-panel adjustable posterior frame 110 or may be attached to the sleeve cover 530 encapsulating the posterior frame 110. As a result, an orthosis, namely a thoracic lumbar sacral orthosis (TLSO), may be formulated by a combination of both the posterior frame 110 and the belt 920. As another embodiment, the belt 920 may be configured to laterally wrap around the covered posterior frame 110.

It should be apparent, however, to those skilled in the art that many more modifications besides those already described are possible without departing from the inventive concepts herein. The inventive subject matter, therefore, is not to be restricted except in the spirit of the disclosure. Moreover, in interpreting the disclosure all terms should be interpreted in the broadest possible manner consistent with the context. In particular the terms "comprises" and "comprising" should be interpreted as referring to the elements, components, or steps in a non-exclusive manner, indicating that the referenced elements, components, or steps can be present, or utilized, or combined with other elements, components, or steps that are not expressly referenced.

What is claimed is:

1. An adjustable orthosis, comprising:
- a posterior frame including at least a first panel and a second panel, the first panel is adjustable in relation to the second panel to convert the posterior frame from at least a first size to a second size; and
- a sleeve for covering at least a portion of an external surface of the posterior frame, the sleeve comprises:
  - an anterior side of the sleeve that includes
    - a first padded area formed of a first material and is structured to be situated in front of an upper portion of an anterior surface of the second panel of the adjustable posterior frame,
    - a second padded area formed of the first material and is structured to be situated in front of a lower portion of an anterior surface of the first panel of the adjustable posterior frame, and
    - an elastic middle area formed of a second material different than the first material and is interposed between and separates the first padded area and the second padded area, wherein the elastic middle area is configured to enable the first padded area and second padded area to retain respective positionings in connection with components of the posterior frame as the posterior frame is moved between a first height position and a second height position,
  - a posterior side of the sleeve, wherein an opening is formed within the posterior side of the sleeve, and
  - a compartment accessible through the opening and formed between an inner surface of the anterior side and an inner surface of the posterior side.

2. The adjustable orthosis of claim 1, wherein the first size corresponds to a first height and the second size corresponds to a second height that is greater than the first height.

3. The adjustable orthosis of claim 1, wherein the adjustable posterior frame including the first panel and the second panel being housed within the compartment.

4. The adjustable orthosis of claim 1, wherein the elastic middle area of the sleeve is configured to expand to a first length to support the adjustable posterior frame in a first position or to expand to a second length greater than the first length to support the adjustable posterior frame in a second position while the first padded area retains its positioning over the upper portion of the anterior surface of the second panel and the second padded area retains its positioning over the lower portion of the anterior surface of the first panel.

5. The adjustable orthosis of claim 1, wherein a first region and a second region of the first material are made of an inelastic material.

6. A sleeve for covering an external surface of an orthosis including an adjustable posterior frame including a first panel slidably coupled to a second panel, the sleeve comprising:
- an anterior side of the sleeve;
- a first padded area that is structured to be situated in front of an upper portion of an anterior surface of the second panel of the adjustable posterior frame;
- a second padded area that is structured to be situated in front of a lower portion of an anterior surface of the first panel of the adjustable posterior frame;
- an elastic middle area interposed between and separating an upper area of the sleeve proximate to the first padded area and a lower area of the sleeve proximate to the second padded area, wherein the elastic middle area is configured to enable the first padded and second padded area to retain respective positionings in connection with components of the posterior frame as the posterior frame is moved between a first height position and a second height position;
- a posterior side of the sleeve, wherein an opening is formed within the posterior side of the sleeve; and
- a compartment accessible through the opening and formed between an inner surface of the anterior side and an inner surface of the posterior side.

7. The sleeve of claim 6, wherein the adjustable posterior frame including the first panel and the second panel housed within the compartment.

8. The sleeve of claim 6, wherein the elastic middle area expands in length to support the adjustable posterior frame in a first position or in a second position at an increased height over the first position while the first padded area retains its positioning over the upper portion of the anterior surface of the second panel and the second padded area retains its positioning over the lower portion of the anterior surface of the first panel.

9. An adjustable orthosis, comprising:

a posterior frame including at least a first panel and a second panel, the first panel is adjustable in relation to the second panel to convert a size of the posterior frame from a first length to a second length greater than the first length; and a sleeve for covering at least a portion of an external surface of the posterior frame, the sleeve comprises:

an anterior side of the sleeve that includes a first padding that is structured to be situated in front of an upper portion of an anterior surface of the second panel of the posterior frame, a second padding that is structured to be situated in front of a lower portion of an anterior surface of the first panel of the posterior frame, and a middle region interposed between and separates the first padding and the second padding, wherein the middle region includes an elastic material wherein the middle region, due the elastic material, is configured to enable the first padding and second padding to retain respective positionings in connection with components of the posterior frame as the posterior frame is moved between a first height position and a second height position, a posterior side of the sleeve, wherein an opening is formed within the posterior side of the sleeve, and a compartment accessible through the opening and formed between an inner surface of the anterior side and an inner surface of the posterior side.

10. The adjustable orthosis of claim 9, wherein the first length corresponds to a first height and the second length corresponds to a second height that is greater than the first height.

11. The adjustable orthosis of claim 9, wherein the adjustable posterior frame including the first panel and the second panel being housed within the compartment.

12. The adjustable orthosis of claim 9, wherein the elastic middle area of the sleeve is configured to expand to a first length to support the adjustable posterior frame in a first position or to expand to a second length greater than the first length to support the adjustable posterior frame in a second position while the first padded area retains its positioning over the upper portion of the anterior surface of the second panel and the second padded area retains its positioning over the lower portion of the anterior surface of the first panel.

* * * * *